(12) United States Patent
Huhtala et al.

(10) Patent No.: US 7,840,346 B2
(45) Date of Patent: Nov. 23, 2010

(54) REAL TIME PERFORMANCE COMPARISON

(75) Inventors: Yka Huhtala, Helsinki (FI); Antti Sorvari, Itäsalmi (FI); Markus Kahari, Helsinki (FI)

(73) Assignee: Nokia Corporation, Espoo (FI)

( * ) Notice: Subject to any disclaimer, the term of this patent is extended or adjusted under 35 U.S.C. 154(b) by 903 days.

(21) Appl. No.: 11/591,872

(22) Filed: Nov. 2, 2006

(65) Prior Publication Data

US 2008/0109158 A1 May 8, 2008

(51) Int. Cl.
G06F 19/00 (2006.01)

(52) U.S. Cl. .................. 701/209; 702/182; 702/189; 702/194; 702/95; 702/142; 702/188; 482/8; 482/900; 340/539.1

(58) Field of Classification Search .......... 701/209; 455/456.2; 342/357.09; 702/182, 189, 194, 702/95, 96, 97, 142, 188; 482/8, 900, 902; 340/539.1; G06F 19/00
See application file for complete search history.

(56) References Cited

U.S. PATENT DOCUMENTS

| | | | | |
|---|---|---|---|---|
| 5,553,007 | A * | 9/1996 | Brisson | 702/182 |
| 6,013,007 | A * | 1/2000 | Root et al. | 482/8 |
| 6,626,799 | B2 * | 9/2003 | Watterson et al. | 482/4 |
| 6,716,139 | B1 * | 4/2004 | Hosseinzadeh-Dolkhani et al. | 482/1 |
| 6,788,200 | B1 * | 9/2004 | Jamel et al. | 340/539.13 |
| 6,960,997 | B2 * | 11/2005 | Gieseke et al. | 340/539.13 |
| 7,254,516 | B2 * | 8/2007 | Case et al. | 702/182 |
| 2002/0173407 | A1 * | 11/2002 | Bowman | 482/8 |
| 2002/0184079 | A1 * | 12/2002 | Nishimoto | 705/10 |
| 2003/0022674 | A1 * | 1/2003 | Shintai et al. | 455/456 |
| 2003/0163283 | A1 * | 8/2003 | O'Brien | 702/160 |
| 2003/0164779 | A1 * | 9/2003 | Gieseke et al. | 340/993 |
| 2004/0046692 | A1 * | 3/2004 | Robson et al. | 342/357.06 |
| 2005/0156719 | A1 * | 7/2005 | Flick | 340/426.19 |
| 2005/0271011 | A1 * | 12/2005 | Alemany et al. | 370/331 |
| 2006/0031126 | A1 * | 2/2006 | Ma et al. | 705/26 |
| 2006/0238347 | A1 * | 10/2006 | Parkinson et al. | 340/572.4 |
| 2008/0188354 | A1 * | 8/2008 | Pauws et al. | 482/8 |

FOREIGN PATENT DOCUMENTS

EP 1 085 683 A1 3/2001

OTHER PUBLICATIONS

Garmin Ltd., Forerunner 205/305 Owner's Manual, May 2006.
U.S. Appl. No. 11/542,038, filed Oct. 2, 2006, Huhtala et al.
Garmin Ltd., "Cyclists Get the Competitive Advantage with Garmin's Edge", Aug. 31, 2005.

* cited by examiner

*Primary Examiner*—Tuan C To
(74) *Attorney, Agent, or Firm*—Ditthavong Mori & Steiner, P.C.

(57) ABSTRACT

Real time performance comparison involves identifying predefined route data corresponding to a route. Measured locations are detected while a user traverses the route carrying a mobile device. The measured locations are sent via a network synchronously with the detection of the respective measured locations. Comparative data points are derived based on the predefined route data and the measured locations in response to receiving the measured locations. The comparative data points are sent, via the network, in response to measured locations. The comparative data points allow the user to measure relative performance during the route traversal.

15 Claims, 8 Drawing Sheets

REAL TIME PERFORMANCE COMPARISON

FIELD OF THE INVENTION

This invention relates in general to mobile devices, and more particularly to providing real time performance comparisons using position detecting mobile devices.

BACKGROUND OF THE INVENTION

The ubiquity of cellular phones and similar mobile electronics has led to demands for ever more advanced features in these devices. Mobile phones are increasingly becoming multipurpose devices. For example, it is becoming much more common for mobile phones to include integrated devices such as cameras and alternate network interfaces (e.g., Bluetooth, Wi-Fi). Another feature that is expected to be included in many future mobile devices is the ability to determine location of the device.

Currently, location detection can be done on a coarse scale using wireless communication infrastructure, such as determining the approximate location based on the base station to which a device is connected. An even more useful form of location detection involves accessing Global Positioning System (GPS) satellites. The GPS system uses a constellation of more than two dozen satellites whose signals can be accessed by receivers on the earth. A terrestrial GPS receiver and associated logic is able to determine its latitude and longitude by triangulating the signals from three satellites. If signals from a fourth satellite can be received, the elevation can also be determined.

For some time, small GPS receiving devices have been available for such purposes as vehicle navigation, outdoor activities, location based gaming, etc. Typically, the GPS receiving devices are incorporated into a standalone device that, in its most basic form, provides a readout of current location. Where memory, displays, and processing power permit, such devices may also include other features, such as map overlays and the storage of waypoints.

As the costs of GPS sensors decrease, they are being incorporated into other devices as well. For example, modern cell phones and Personal Digital Assistants (PDAs) have become ubiquitous, general-purpose, mobile data processing devices. Given the mobility and always-on nature of such devices, it is quite natural that these devices will include GPS receivers and similar device so that the users can to take advantage of location-aware data-processing applications. For example, the currently available Nokia® N95 model cellular phone includes an integrated GPS sensor. In addition, such mobile devices are capable of accessing data networks, and this network access can enhance location-aware processing. The present disclosure describes improved location-aware methods and devices that provide advantages over existing implementations.

SUMMARY OF THE INVENTION

To overcome limitations in the prior art described above, and to overcome other limitations that will become apparent upon reading and understanding the present specification, the present invention discloses a system, apparatus and method for real-time performance comparison using mobile devices. In accordance with one embodiment of the invention, a method involves identifying predefined route data corresponding to a route. Measured locations are detected via a location sensor while a user traverses the route carrying the location sensor. The measured locations are sent to a network service synchronously with the detection of the respective measured locations. Comparative data points are received from the network service in response to measured locations sent to the network service. The comparative data points are derived based on the predefined route data and the measured locations. The comparative data points allow the user to measure relative performance during the route traversal.

In more particular embodiments, identifying the predefined route data may involve selecting the predefined route data via the network service. Receiving the comparative data points may involve receiving statistics relative to other users who have traversed the route. In such a case, the method may further involve displaying, based on the statistics, relative locations of the user and the other users on a map of a mobile device carried with the user. Receiving the relative statistics may involve receiving a ranking of the user relative to the other users who have traversed the route. Determining the ranking of the user relative to the other users who have traversed the route may involve calculating the ranking based on times to reach a checkpoint on the route.

In other, more particular embodiments, receiving the comparative data points from the network service involves receiving the comparative data points at a mobile device carried by the user while traversing the route, and wherein the method further involves rendering the comparative data points to the user via the mobile device during route traversal. Rendering the comparative data points to the user via the mobile device during route traversal may involve rendering a sound to the user that describes the comparative data points and/or rendering a map display to the user that shows the comparative data points.

In another embodiment of the invention, a method involves identifying predefined route data corresponding to a route, and receiving, via a network, measured locations detected by a user traversing the route. The measured locations are received synchronously with the detection of the measured locations. Comparative data points are derived based on the predefined route data and the measured locations. The comparative data points allow the user to measure relative performance during the route traversal. The comparative data points are sent, via the network, in response to receiving the measured locations during the route traversal.

In more particular embodiments, identifying the predefined route data involves receiving the predefined route data from the user contemporaneously with traversing the route. Deriving the comparative data points may involve deriving statistics relative to other users who have traversed the route, and deriving statistics may involve determining a ranking of the user relative to the other users who have traversed the route. Determining the ranking of the user relative to the other users who have traversed the route may involve calculating the ranking based on times to reach a checkpoint on the route.

In another embodiment of the invention, an apparatus includes a data interface capable of interfacing with a location sensor and a network interface capable of communicating with a network service. A processor is coupled to the data interface and the network interface, and a memory is coupled to the processor The memory includes instructions that cause the processor to: identify predefined route data corresponding to a route; detect, via the location sensor, measured locations while a user traverses the route carrying the location sensor; send the measured locations to the network service synchronously with the detection of the respective measured locations; and receive from the network service comparative data points in response to measured locations sent to the network service. The comparative data points are derived based on the predefined route data and the measured locations, and allow the user to measure relative performance during the route traversal.

In more particular embodiments, the instructions cause the processor to identify the predefined route via the network service. In one arrangement, the comparative data points include statistics relative to other users who have traversed the rout. The apparatus may further include a display, and the instructions cause the processor to render on the display, relative locations of the user and the other users, based on the statistics. The relative statistics may include rankings of the user relative to the other users who have traversed the route.

In other, more particular embodiments, the apparatus may further include a user output device, and the instructions cause the processor to describe the comparative data points to the user via the user output device during route traversal. The user output device may include a speaker and/or a map display.

In another embodiment of the invention, an apparatus includes a network interface capable of communicating with a mobile device that detects measured locations while a user of the device traverses a route. A processor is coupled to the network interface, and a memory is coupled to the processor. The memory includes instructions that cause the processor to: identify predefined route data corresponding to the route; receive the measured locations from the mobile device synchronously with the detection of the measured locations by the mobile device; derive comparative data points based on the predefined route data and the measured locations, wherein the comparative data points allow the user to measure relative performance during the route traversal; and send the comparative data points to the mobile device during the route traversal.

In more particular embodiments, the instructions cause the processor to receive the predefined route data from the mobile device contemporaneously with the route traversal. Deriving the comparative data points may involve deriving statistics relative to other users who have traversed the route Deriving statistics relative to other users who have traversed the route may involve determining a ranking of the user relative to the other users who have traversed the route, which may further involve calculating the ranking based on times to reach a checkpoint on the route.

In another embodiment of the invention, a computer-readable medium has instructions which are executable by a data processing arrangement for performing steps that include: identifying predefined route data corresponding to a route; obtaining measured locations that are detected while a user traverses the route carrying a mobile device; facilitation transmission of the measured locations via a network synchronously with the detection of the respective measured locations; and facilitation transmission, via the network, comparative data points in response to transmission of the measured locations, wherein the comparative data points are derived based on the predefined route data and the measured locations, and wherein the comparative data points allow the user to measure relative performance during the route traversal.

In more particular embodiments, obtaining the measured locations involves receiving the measured locations via the network from a mobile device that detects the measured locations, and the steps further involve deriving the comparative data points based on the predefined route data and the measured locations. In another more particular embodiment, obtaining the measured locations involves detecting the measured locations via a location sensor coupled to the data processing arrangement, and the steps further involve rendering the comparative data points to the user via the data processing arrangement during route traversal.

In another embodiment of the invention, a system includes: means for identifying predefined route data corresponding to a route; means for detecting measured locations while a user traverses the route carrying a mobile device; means for sending the measured locations via a network synchronously with the detection of the respective measured locations; means for deriving comparative data points based on the predefined route data and the measured locations in response to receiving the measured locations; and means for sending, via the network, the comparative data points in response to measured locations, wherein the comparative data points allow the user to measure relative performance during the route traversal. The system may also include means for rendering the comparative data points to the user during the route traversal.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described representative examples of systems, apparatuses, and methods in accordance with the invention.

BRIEF DESCRIPTION OF THE DRAWINGS

The invention is described in connection with the embodiments illustrated in the following diagrams.

DETAILED DESCRIPTION OF EMBODIMENTS OF THE INVENTION

In the following description of various exemplary embodiments, reference is made to the accompanying drawings that form a part hereof, and in which is shown by way of illustration various embodiments in which the invention may be practiced. It is to be understood that other embodiments may be utilized, as structural and operational changes may be made without departing from the scope of the present invention.

Generally, the present invention involves using a network service to generate comparative data that can be presented in real-time or near real-time to a user based on location measurements, such as Global Positioning System (GPS) data measurements. This comparative data may be particularly useful in such applications as assisting with sports and fitness activities that involve traversing distances over time. Although various embodiments may describe the use of GPS in measuring location, time, speed, and/or other data, the present invention is not limited to GPS. For example, future satellite based systems, such as the European Galileo satellite navigation system, may be able to provide position data as well. In addition, various non-satellite based location measurements may also be used, such as cellular base station triangulation, location beacons, inertial navigation, etc.

Sports and fitness activities can be monitored with location sensing (e.g., GPS assisted) devices in order to measure speed and distance. This speed and distance data is recorded, and can be used myriad ways by sports aficionados. For example, careful measurement of distances and times are important for runners and bicyclists who are trying to track progress and improvements as part of an exercise regime. Although concepts described herein are shown being applied to fitness, activities, this data may be useful in a wide range of endeavors. For example, such data may be used in vehicular racing, measuring commute data, tracking shipments, and any other activity involving comparing distances and times between non-simultaneously occurring activities or events.

GPS-based sports monitoring devices provide a way of measuring speed and distance during a workout or other activity, and also can be used in creating detailed location and time records. Performance comparison is a useful feature on those devices. For example, a GPS exercise device may make it possible for the user to create performance targets by setting a target distance and time. Such values as estimated time of completion may also be calculated using these devices. Typically, such calculations are made by assuming that the target route is flat and that the exerciser would maintain a steady pace throughout the route. However, such a solution may be unsatisfactory for a number of reasons. First, hills and other obstacles may vary the pace of the user. Further, by ignoring changes in elevation, significant errors may be introduced into distance measurements. Another source of error is introduced by the tendency of GPS signals to drop in and out. If a device is out of range for significant amounts of time, particularly on complex portions of a route, any-estimates made by "connecting the dots" between subsequent readings may ignore significant features of the route.

Therefore, in order to accurately track performance targets and other data, a device according to an embodiment of the invention may be able make comparisons with previously known route data. Such route data may take into account the profile of the route, including changes in elevation. This route data may have been previously recorded by users who have previously traversed the route, and/or may be obtained from other sources known to be accurate. Other route data used for the comparison may be user-specific, such as intensity measures (e.g., heart and breathing rates) made from workouts previously recorded by the user on the same or similar paths.

Any combination of known route data and previously recorded workout(s) on a particular route can be used to compare sports performance in real time using a mobile device. A "workout" as described herein may involve determining an ordered set of location points, typically via GPS measurements. In addition to the location information, each workout location point may contain time information. The time and location information may be used to derive for each measured point elapsed times ad distances from the start of the workout to the point. The workout location point data may also include other measurements, such as heart rate, altitude, slope, environmental conditions (e.g., temperature, wind), and any other sensor data that can describe the intensity or conditions of the workout.

A "route" is generally an ordered set of location points. A route can be derived from existing databases, such as maps, survey data, etc. The route can also be user-created. User-created route data may be currently or previously recorded by the user, received from another person (e.g., downloaded as a file), created manually with a phone/PC software, and/or downloaded from a dedicated service. A single route can be associated with several recorded workouts. The workout can be attached with more general information about the exercise, for example, the type of exercise. The type can be related to exercise intensity (e.g., hard, medium, low) type of activity (e.g., walking, running, cross country skiing), etc. Any data that characterized previously recoded workouts can be applied to and compared with a current workout.

Although both routes and workouts may be described herein as ordered sets of points, those skilled in the art will appreciate that alternate data structures and geometric methods may be used to model routes and workouts for purposes of performance tracking. For example, routes and workouts may be described as mathematical functions, such as curve fitting, Fourier series, least squares fit, etc. In another example, route and workout data could be represented as a start point in geo-coordinates, followed by an ordered list of deltas from the start point. The performance tracking embodiments described herein are independent of any particular representation of discrete or continuous data.

Among other things, a device according to an embodiment of the invention can utilize route data and other workout data to complement the currently measured workout data, such as performing a real-time comparison of the measured data with the route/workout data via the device. In one arrangement, when starting to exercise, the user selects the route and the target workout. The target workout can be selected in different ways. The system can suggest for example, the fastest workout on route, an average paced workout on route, based on other intensity measure, or according the goal of the current workout. The intensity measure can be based on, for example, average heart rate or the type of the workout (e.g., hard, medium, low). In another arrangement, the goal of the current workout could be to beat a personal best by selecting the best previous performance on the selected route for comparison. In yet another arrangement, the comparison workout can be a live or time-shifted, ongoing or recorded, workout of another user that can be tracked by the user in real time, thereby setting up a "virtual race" with other people.

After selection of the route and target workout, the user starts moving and recording the current workout. Based on the selected route and selected target workout, the system can now calculate:

a. user's current location on the route;
   b. target workout's location on the route at the current time;
   c. target workout's time at the user's current location;
   d. user's estimated time and distance of arrival to finish; and
   e. target workout's estimated time and distance of arrival to finish Using a, b, and c from above, the time and distance gap between the user and the target workout can be calculated. This calculation can be made when the user moves and receives a location point from the location device, or on any moment of time during the workout. The user can use this data to pace their workout, and provide motivation to continue or put in an extra effort. An example of how this can be accomplished is shown in FIG. 1.

Figure 1:
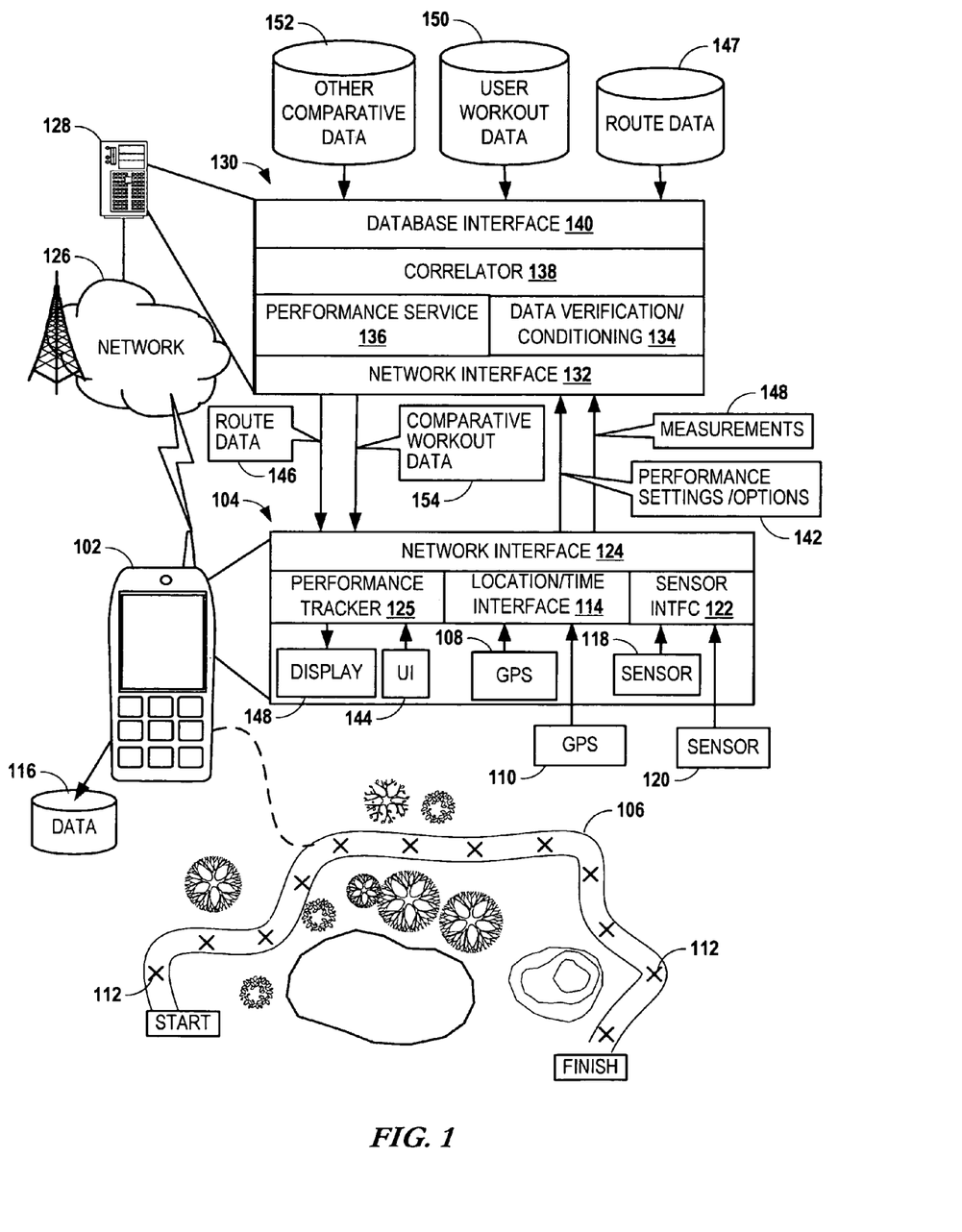
FIG. 1 is a block diagram of a system according to embodiments of the present invention.

The diagram in FIG. 1 illustrates an example of route-assisted GPS tracking according to an embodiment of the invention. A mobile terminal 102 (here shown as a cellular phone) includes a performance tracking arrangement 104 that may include hardware and software components. A user carries the terminal 102 when traversing a path 106, such as during a workout. The terminal 102 measures a number of data points that may be associated with waypoints 112 along the path. The terminal 102 may include an integrated GPS sensor device 108 and/or interface with an external GPS device 110 to measure location data associated with the waypoints 112. The location data measured via these GPS devices 108, 110 can be received at the terminal 102 via a software interface 114, and can also be stored on a memory 116 of the device 102.

The part of data 116 that measured via the location/time interface 114 may include a latitude, longitude, elevation, time, and quality of location fix for each waypoint 112 of the workout. The data 116 may also include other measurements made during the workout, such as via internal or external sensors 1118, 120 which send data to the terminal 102 via a sensor interface 122. For example, the sensors 114, 116 may be able to measure such conditions as air temperature, relative humidity, tilt, acceleration, heart rate, breathing rate, body temperature, etc. Any combination of these sensor measurements can be made simultaneously with time and location data measured at each of the waypoints 112, and can be used to gauge aspects of physical performance along the route 106. The data 116 may also include data that is derived/calculated/estimated from sensor data at the mobile terminal 102. For example, sensed heart rate data can be used to estimate Metabolic Equivalents (METS), Excess Post-Exercise Oxygen Consumption (EPOC), calorie consumption, etc. The intensity/performance data can be also calculated at the service side 130 instead of (or in addition to) being calculated via the mobile terminal 102

Generally, the measured data 116 can be stored in persistent memory for future reference. However, in order to track performance in real-time, the data 116 is also compared to other data via the performance tracking arrangement 104. For performance tracking, the measurements need not be stored in persistent storage, but may at least be buffered in random access memory on the device 102. In the illustrated arrangements, the data received via sensor interfaces 114, 122 is processed via a network interface 124 that is capable of being communicating via a network 126.

The network interface 124 of the mobile terminal 102 allows the performance tracking arrangement 104 to provide real-time, performance comparison data. The control and display of this data may be facilitated via a performance tracking application 125. The performance tracking application 125 may perform some operations locally (including user interface and sensor processing) and provide some options with the aid of a network entity, as represented by server 128. The server 128 includes a network service module 130 with a network interface 132 capable of communicating via the network 126 with network elements such as the terminal 102. The service module 130 also includes a data verification/conditioning module 134, a performance service interface 136, a correlator 138 and a database interface 140. The components of the service module 130 may be any combination of hardware and software, and may include functionality that is distributed across many network entities.

The performance service module 130 may be configured to provide some of the general setup functions that govern the interactions between the terminal 102 and service 130. For example, the terminal 102 may allow the user to manually select options 142 related to the workout, including routes and comparative workout data. These selections can be made via a user interface 144 of the terminal 102 and sent via the respective network interfaces 124, 132. Other settings 142 may be automatically determined and sent by the terminal 102 without requiring user interaction. For example, the location module 114 may send a currently sensed location (if available) to the service module 130 as part of an initial connection and negotiation. This location data may be used to automatically select routes and comparative data.

Generally, the verification/conditioning module 134 may act as a standard interface for receiving sensed data from remote terminals, both for purposes of setup/configuration and for performing real-time performance tracking functions. The correlator module 138 receives and interprets this conditioned data from the verification/conditioning module 134. For example, the correlator module 138 may be able to automatically determine a likely selection of route data based on initial coordinates received during service initiation.

The correlator module 138 may also perform data transformations that allow diverse sets of data to be compared. For example, route and workout data may be stored as discrete points indexed by time or location, however the discrete steps between two different sets of data may not have the same type or spacing of index steps. For example, one set of data may have points measured every 10 meters from the start of the route/workout, and another may have had points measured at one second intervals at non-constant speeds from the start of the workout. Therefore, the correlator module 138 may perform operations such as interpolation or extrapolation to be able to compare various data sets. Data normalization may also be performed via the data verification/conditioning module 134, which may place all incoming data in a normalized or standard format before sending the data to other components of the service 130.

One function provided by the service 130 may be to provide or identify route data 146 for use by the terminal 102 during workouts. This route data 146 may be already stored locally on the terminal 102, such that the service 130 merely identifies the correct route on behalf of the performance tracker 125. Alternatively the route data 146 may be obtained via a database 147 that is accessible to the service 130 via the database interface 140. This route data 146 may have many uses before, during, and after the workout. For example, a graphic representation of the route may be shown on a display 148 of the terminal 102 before the user begins to exercise. When the user begins the workout, a continuously updated current location indicator may be overlaid on the illustrated route. The route data 146 may also be used to categorize currently collected data, e.g., used in forming a name and storage location (e.g., folder/directory) for the data.

Once the service 130 and performance tracking arrangement 104 have been configured, the user begins to workout carrying the terminal 102 and/or sensors 110, 120. The data 148 that is measured via the sensor interfaces 114, 122 is sent to the service 130 via the terminal's network interface 124. The performance tracker service 125 may facilitate this sending of measured data 148, or the measured data 148 may be sent by some other program running on the terminal 102. In response to the measurement data 148, the service 130 processes the data 148 via the data verification/conditioning module 134 and correlator module 138.

One function provided by the correlator module 138 and/or performance service 136 is to compare current measurements against other workout data. This comparative data may be derived from other users and stored in a commonly accessible location, as exemplified by the user workout database 150. Other relevant data may also be used in this correlation process, as exemplified by the other comparative database 152. For example, the other comparative data may relate to statistical data, such as the user's percentile performance in the current activities when compared to a statistical average of others in their particular age and weight group. Some comparisons could be made for safety reasons, such as warning the user of an increased risk of hypothermia or some other health risk based on currently sensed conditions. Other comparisons could be for amusement, such as comparisons with the performance of animals or machines.

Based on initial settings and configurations, the performance service interface 136 can deliver comparative workout data 154 to the terminal 102 for the benefit of the user. This data 154 may be adapted for display 148 (e.g., overlay on a map), graphical indicator (e.g., bar graphs), textual display, or any other manner of graphical representation known in the art. The data 154 may also be communicated via other transducers, including by sound and touch.

In the arrangements described above, the terminal device 102 is carried with the user while traversing the path. In another arrangement, the external device 110 and/or sensor 120 may be carried with the user and the device 110 and/or sensor 120 records the data in its own memory and/or transmits it to the terminal 102 in real-time. For example, the terminal 102 and external devices 110, 120 may be able to communicate via short- or medium-range wireless communications. The terminal 102 may be placed in a car, for example, and the user carries the smaller sensing devices 110, 120 while on the workout. In order for the user to gain real time feedback of performance via the performance tracker application 125, the devices 110, 120 may include their own user output interfaces, such as display or headphone interfaces.

Figure 2:
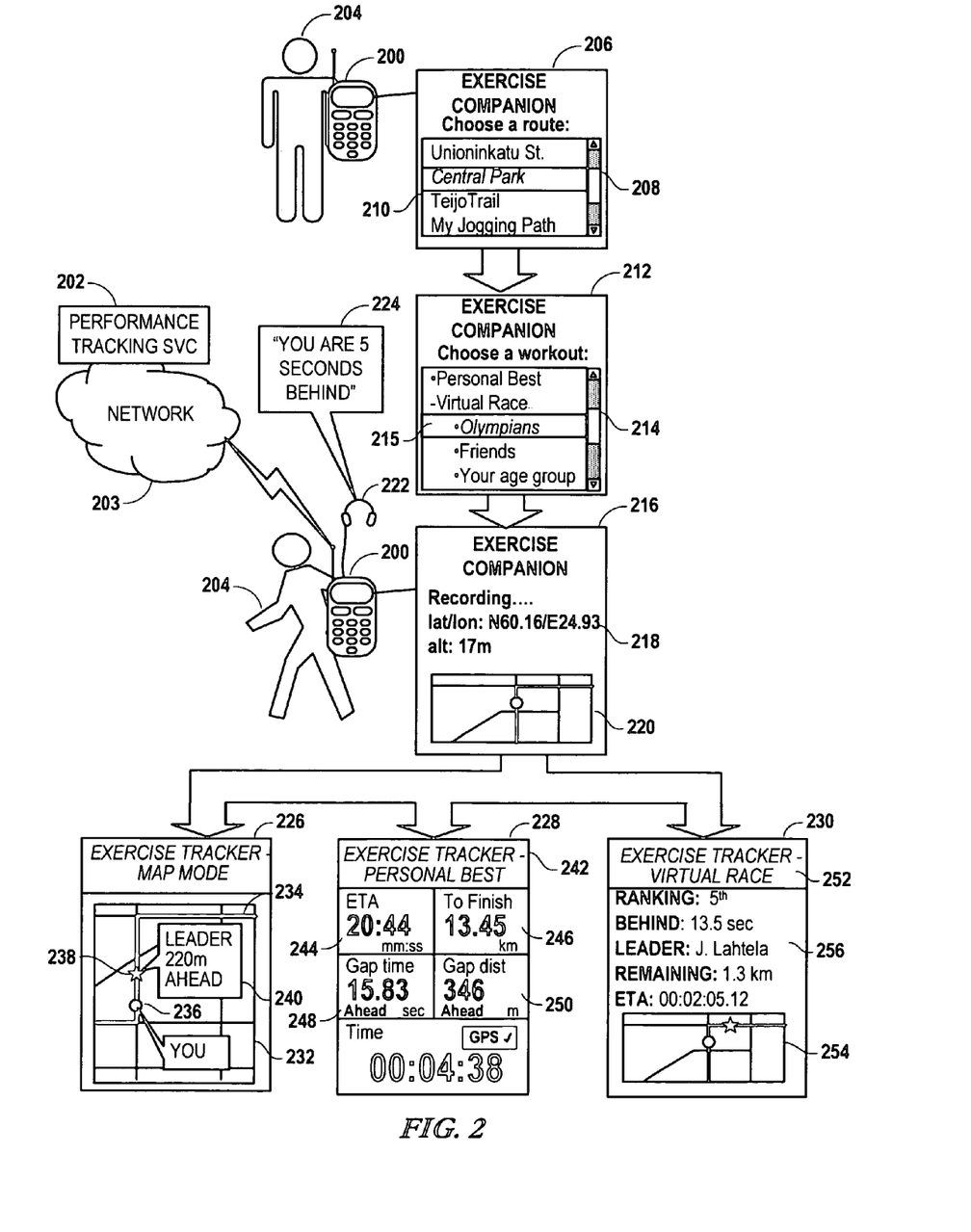
FIG. 2 is a diagram showing sequences of using route-assisted location sensing according to embodiments of the present invention.

In reference now to FIG. 2, a more particular example is shown of how a mobile device 200 may utilize a performance tracking service 202 via a network 203 according to embodiments of the invention. A user 204 includes the mobile device 200 as part of an activity for which performance tracking is desired. The route on which the activity to be undertaken is typically selected before the activity has begun, as seen in user interface display 206. In this display 206, the user is presented with a list 208 of possible routes, from which one route 210 is selected.

The selection of routes 208 may occur before or after the user 204 connects to the service 202. In one arrangement, the list 208 represents locally stored routes that the user 204 is familiar with by name. In such an arrangement, the list 208 can be filtered from a larger list of possible routes based on local inputs. Those local inputs may include user-generated inputs (e.g., names or portions thereof typed or spoken by the user), and may also include location inputs from a location tracker (e.g., GPS sensor) in the mobile device 200. Other forms of inputs may be alternate proximate locations sensors, such as cellular base stations, wireless local area network access points, or any other short range transmitter proximate to the area of interest. Based on these inputs, the size of the list 208 may be reduced to ease selection tasks (e.g., scrolling) required by the user 204.

Although the mobile device 200 may be able to store a large quantity of routes, a much larger selection may be made available via private or publicly accessible networks 203. Therefore, in another example, the list 208 could be obtained via the service 202, either by a download of route data or metadata, or in assisting the device 200 to locate locally cached route data that is appropriate. As with local selection mechanisms, selection of routes via the service 202 may involve any combination of manual user selection of route parameters and automatic selection based on sensor inputs. It will be appreciated that the list data 208 ultimately presented to the user 204 may include a combination of locally stored or remotely accessed route data. For ease of use, it may be preferable to eliminate distinctions between remote and local data when presenting the list 208 to the user 204. In other arrangements, it may be desirable to delineate between remote data sources and local data sources, including those local sources that were locally created, or downloaded/cached from elsewhere. This later arrangement may be preferable where the device 200 has access to networks with limited or expensive bandwidth.

After the user 204 has selected the current route 210, the user 204 may also wish to select workout data for purposes of comparing to the current workout. This is represented in screen 212, which shows a list 214 of target workouts available for the selected route 210. Generally, the target workouts 214 may be calculated or measured for specific routes, and be uniquely associated with that route. An example of this is where the user 204 has repeatedly traversed the route, and the current workout target is the user's personal best time. The target workouts may be been measured for other people as well. Alternatively, some the target workouts 214 may be based on generic data, and set of target workout data is generated for any route fitting certain parameters. An example of this is where the selected route 210 is a 10 km run, and the target workout is generated based on the user 204 or some other person's performance on a different 10 km run. The target workout generated in this way may include adjustments for various factors, including elevation, surface type, temperature, wind, etc., so that the target data is a realistic simulation of how that person might perform on this route 210, even if that person had never set foot there.

The list 214 of target workouts may be suggested based on locally stored data, or it can be suggested online from the service 202. The list 214 may also include a selection labeled "None" or similar to indicate that no target workout data is to be used. As indicated in this screen 212, the user has selected workout 215, which is a comparison with the performance of an Olympic athlete.

After the route and target workout selections are made, the user 204 starts the workout, as indicated by screen 216. The illustrated screen 216 is an initialization screen, showing typical current workout data such as current location 218 and a graphical representation of the route, such as map 220. In addition to this displayed data 218, 220, the device 200 can provide the user 204 with other outputs comparing the current measured data with the selected workout data 215. For example, the device 200 may include a speaker or headphones 222, and the user 204 is provided with regular audio indications 224 of comparative data. The audio indications 224 can be triggered by certain time/distance intervals, or by changes that exceed a minimum threshold. In this example, the audio indications 224 include spoken text, such as pre-recorded speech or speech generated by a voice synthesizer. In other examples, the audio indications 224 may include synchronization tones for pacing, tones that increase in frequency the closer that the user 204 gets to some target (e.g., similar to sonar feedback), descriptions of route milestones, etc.

In addition to audio feedback 224, the device 200 may be able to provide various types of visual feedback, as represented by screens 226, 228, and 230. Screen 226 includes a map 232 with graphical representations of the route 234 and the user's current location 236 overlaid on the map. Also shown on the map 232 is an icon 238 that represents a workout target, in this case the location of the same workout performed by the user 204 or someone else, or some theoretical target. The map 232 could include multiple targets 238 shown both ahead of and/or behind the current location icon 236, thereby simulating a race between multiple people. A label 240 shows metadata related to the target icon 238, such as distance ahead in this example.

The comparison of data on the map 232 provides the user 204 with a graphical representation of the current workout compared to target workout(s). Similar information may also be shown in an alphanumeric form, as seen in the screen 228. As the title block 242 indicates, this screen is showing a comparison between the current workout and a previous workout. The displayed data may include data derived solely from the route data and current workout measurements, such as the estimated time of arrival 244 and estimated distance to finish 246. Other data, such as the gap time 248 and gap distance 250 are compared to another targeted workout. The types of data shown in the display 228 may be user configurable, and the data in the display 228 may rotate through a number of different data sets, such as biometric data, environmental data, etc.

Display 230 combines both the graphical map data of screen 226 with the textual data of screen 228. As indicated in the title block 252, the screen 230 presents a "virtual race" that compares the current workout data with that of competitors. A map section 254 and textual/numerical readouts 256 provide a composite view of graphics and statistics, thereby simulating a race against another person. It will be appreciated that any combination of textual and graphical components of the screens 226, 228, and 230 may be used to form a display. Other graphical forms, including line graphs, bar charts, pie charts, area charts, histograms, tables, scatter plots, etc., may be used to compare current workout data with target workout data. For example, a graph or chart may track METS (metabolic equivalents, which is a measure of energy expenditure) of the current workout compared to other workouts.

The workout data provided by these and other displays 226, 228, 230 may be used to motivate the user to perform better or to complete a workout. Such data may also be used to help the user 204 achieve a desired goal or avoid unintended consequences. For example, if workout intensity measures are used in comparison, the system could inform the user 204 to slow down or speed up the workout. Intensity measures may also be used to alert the user 204 to stop or turn back if the workout is too hard compared to the target workout. Such may be the case if it is apparent that the user 204 is not able to finish the route, or at least not be able to finish the route with an intensity level that would be in line with the set target. In cases where the goal is to only indicate whether the user can beat the target parameters, such warnings can be turned off or omitted.

As described above, display 230 presents a readout of a "virtual race." Such a virtual race could be set to run manually or automatically for known routes. For example, at each new location point measured by the device 200, the measured information is sent to the service 202. The service 202 can use this data to calculate user's location on the route. The service 202 can also calculate every workout location on the route that exists in the service 202. As a result, the service 202 knows how the user 204 performs against all the workouts stored in the service 202. This "leader board" information can be send back to the user 204. Now the user 204 knows, for example, that she/he is currently on 5th place on overall results, 10 seconds behind the $4^{th}$, and 13.5 seconds behind first place.

Figure 3:
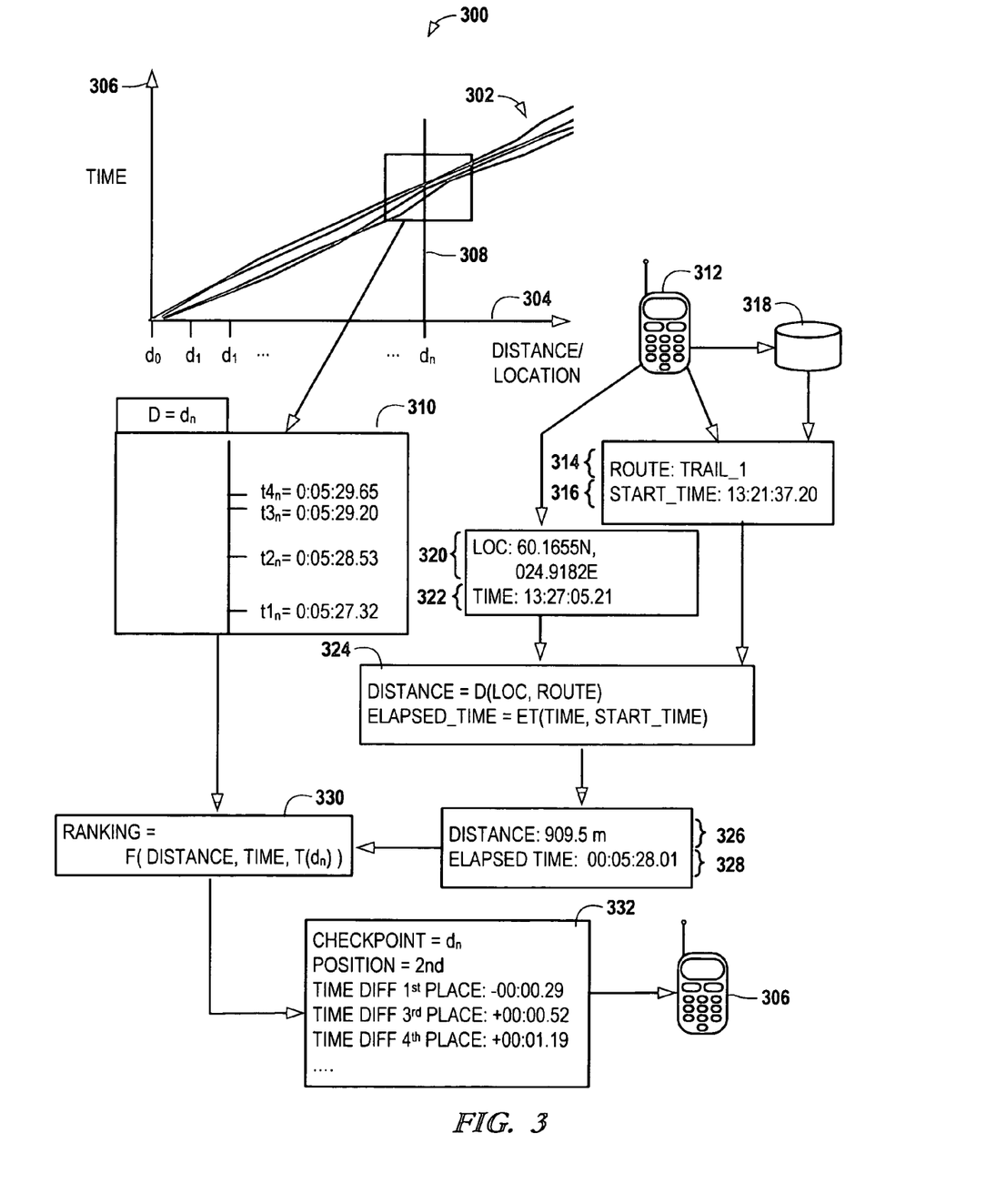
FIG. 3 is a diagram illustrating an example of calculating route comparisons according to an embodiment of the invention.

In reference now to FIG. 3, a diagram provides additional details of how a service according to an embodiment of the invention may provide comparative data so that a mobile device can provide a "virtual race" experience to a user. Generally, a computer or network service tracks a plurality of workout data sets, as represented by line graph 300. This particular graph 300 shows time versus distance on a route, although the concepts described in relation to this graph 300 may be applicable to other combinations of workout data described herein. The use of a line graph 300 to represent workout data is merely for illustration; many alternate forms of representing workout data are known in the art. In particular, workout data is typically stored and accessed in formats that are more conducive to computer solution than graphs, such as arrays, ordered lists, linked lists, binary trees, etc.

The graph 300 contains a number of plots 302 that represent particular workouts. The distance axis 304 may represent linear distance along a route (or some other measure of location), and the time axis 306 represents the time relative to the start of the workout when each distance was reached. Therefore, for any distance $d_n$, the intersections of the plots 302 with a vertical line 308 at distance=$d_n$ results in a collection of times for each instance of the workout, as seen in block 310. Therefore, when a current user measures a distance and elapsed time corresponding to $d_n$ using a mobile device 312, a comparison between the plot points 310 can be made.

The mobile device 312 may measure relative or absolute positions on the route, and/or may also calculate the elapsed distance along the route by itself. Of particular use in calculation of distance based on geocoordinate measurements is accurate route data. Real-time GPS location measurements sometimes contain erroneous or missing data due to signal dropouts. Therefore, a measured data point can be compared to route geometry that is known to be accurate, and thus distances can be more accurately estimated for any given measurement. Thus if the device 312 measures elapsed distance on its own, route data may be stored on or downloaded to the device 306. Alternatively, the mobile device 312 may just send locations and times to network service, and let the service calculate distances.

In the scenario illustrated in FIG. 3, the device 312 sends a route indicator 314 and start time 316 to the service at least once. The route indicator 314 provides a geometric framework that either the device 312 or service can use to interpret subsequent location measurements and for association of target workout data. If the device 312 is configured to determine elapsed time, then the start time 316 may not be needed. The route indicator 314 and time 316 (if needed) may need to be sent only once by the device 312, and can be cached in memory and/or in a data storage 318 that is accessible by the service.

During the workout, the mobile device 312 repeatedly sends current location and time measurement data, as exemplified by location and time measurements 320, 322. The time measurement 322 may be absolute time (as shown) or may be elapsed time from the start of the workout. Based on the current measurements 320, 322 and initial data 314, 316, the service can determine distance and elapsed time of the point, as indication in calculation block 324. The distance traveled is a function of the route geometry 314 (which generally includes a predefined start point) and the current location measurement 320. The elapsed time is a function of the start time 316 and measurement time 322, assuming that these are absolute time measurements. The output of the calculation block 324 is an estimate of distance traveled 326 and elapsed time 328 for the current point.

In the illustrated arrangement, the elapsed distance 326 and time 328 are used with the workout data 300 in order to perform calculation 330 that determines ranking with the other virtual competitors. The elapsed distance 326 determines the location along the x-axis 304 of the data set 300, and the elapsed time 328 is compared with the other times 310 at this particular distance $d_n$. The resulting comparison data 332 based on this calculation may contain numerical rankings, time offsets from other competitors, and other comparative data of interest. The resulting data 332 is sent to the mobile device 312 for rendering to the user as described elsewhere herein. It will be appreciated these illustrated calculations can be undertaken on either the device 312 and/or a network service as appropriate. Although none of the illustrated calculations are particularly intensive by modern processor standards, the accessing of large comparative data sets 300 may make it desirable to institute those parts of the calculation via a network service.

The type of data 332 provided by a system according the embodiment of the invention may vary depending on user preferences and the type of comparison data 300 available. For example, actual or simulated workouts to which the user's current workout is compared can be selected using one or more of the following criteria: 1) Performance time based selection such as workouts from the last n days, weeks months or workouts from the same week, month from the past years (to compensate for seasonal effects); 2) Age group based selection (to e.g. compete against others in the same age group); 3) Performance level based selection (e.g. beginner, advanced, professional); and 4) Male/female selection.

As described above, the workouts can be compared with others in a "virtual competition." As an example, consider a user that has arrived to New York and decides to go exercising in Central Park. The user connects to the Sports Service and downloads a "Central Park 5 km" route to her/his phone. The user starts the workout and during the workout she/he is able to see her/his current position on virtual competition on the Central Park 5 km route and how much she/he is behind/ahead of the all time leader on that route. Users with web browser connected to service, can see in real time how the virtual competition on that route is developing. They can see for example, the all time leader board, this week's fastest, and best cyclists on that route, etc.

There are advantages in utilizing a network service for creating, modifying, and accessing route and workout data. One advantage is that contributions from numerous people can create a rich and diverse set of data usable for workouts. As such, the data received and processed by a network service may be formatted into particular standard formats. Additionally, relationships between types of data may be expressed programmatically and/or via database schemas. In reference now to FIG. 4, a Unified Modeling Language (UML) diagram 400 shows relationships between classes that may be used to represent structures, functions, and relationships of data according to an embodiment of the invention. The two basic classes that may be implemented are those of the Route 402 and Workout 404. Although the Route 402 is shown as a concrete class and the Workout 404 as an abstract class, it will be appreciated that other variations of these classes may be used.

Figure 4:
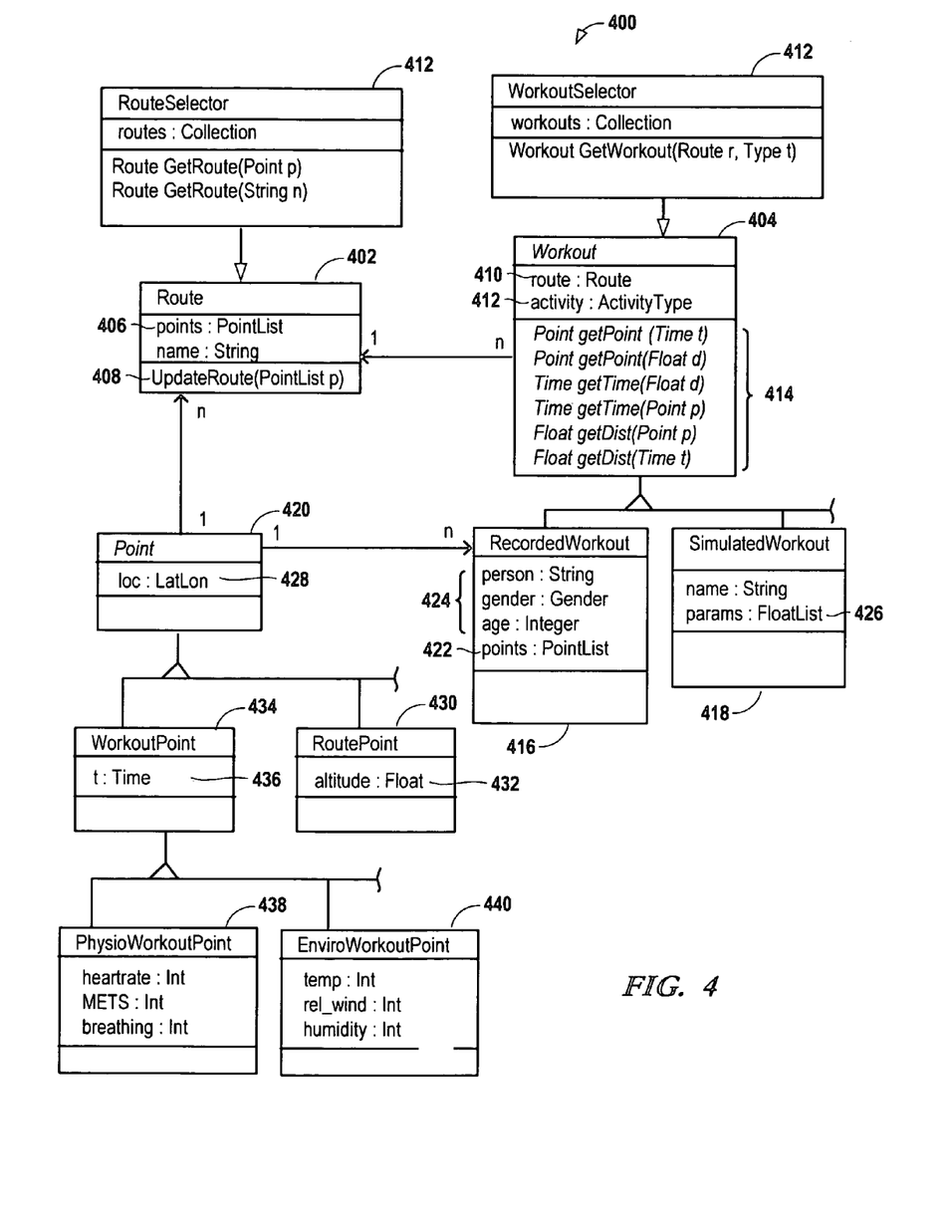
FIG. 4 is a class diagram illustrating relationships between data and functions for route comparisons according to an embodiment of the invention.

The Route class 402 includes a list of points 406 that describe the geometry of a particular route. The points 406 are instantiation of the abstract Point class 420, which will be discussed in detail further below. The Route class 402 may also include a method 408 that allows this geometry to be updated, such as via measured points in a Workout 404 object. The Workout class 404 is associated with a particular route, as indicated by the route data member 410. The Workout class 404 may also have an activity type indicator 412 that may help differentiate between different types of activities. For example, there may be both bicycling and running Workout objects 404 associated with the same Route object 402.

The Workout class 404 includes methods 414 for obtaining various parameters such as geolocation points, elapsed times and elapsed distances based on any of the same, other parameters. In this way, any of these parameters of a current workout can be obtained for easy comparison. Because the Workout class 404 is abstract and does not specify any of the underlying data structures used to define the workout, these methods 414 are also abstract, and would be implemented in concrete classes, such as the RecordedWorkout class 416 and SimulatedWorkout class 418.

The RecordedWorkout class 416 corresponds to data that is typically obtained by GPS or other location sensing apparatus that makes discrete measurements along the member route 410. As such, the RecordedWorkout 416 class may include a list of Point objects 420, as seen in "points" data member 422. Because the RecordedWorkout objects 416 are typically associated with individuals, descriptive information 424 about that individual may also be included.

In contrast with the RecordedWorkout class 416, the SimulatedWorkout class 418 does not need to correspond to an actual workout that took place on the member route 410, and may use mathematical formula and other data to produce the outputs of the member methods 414. This other data is represented by a parameter list 426, which may include, for examples, coefficients of a parametric equation used to generate the resulting values.

As mentioned above, both the Route 402 and Workout 404 classes may use variations on the Point class 420, which at least includes a location variable 428 that, for example, may be expressed as a latitude and longitude. The Route class 402 deals with pure geometry, and therefore may only require a concrete class, shown here as the RoutePoint class 430, that adds and additional geometry component, that of altitude 432. However, the Workout class 404 includes a time component, and may use a specialized WorkoutPoint concrete class 434 that has time member variable 436. As described herein, workout data may include other performance or environmental data that is used in comparisons. Therefore, addition concrete classes PhysioWorkoutPoint 438 and EnviroWorkoutPoint 440 may inherit from the WorkoutPoint 434 and contain additional variables that capture this type of data.

Although the above example utilizes the concept of object oriented relationships, the concepts described in FIG. 4 need not be implemented in an object oriented programming environments. Additionally, the classes shown in the diagram 400 may also have separate or integrated user interface and database components. In particular, a separate but related database schema may be devised to store data related to the classes 400 for efficient storage, retrieval, and query.

Many types of apparatuses may be able to provide network service assisted workout comparisons as described herein. Mobile devices are particularly useful in this role. In reference now to FIG. 5, an example is illustrated of a representative mobile computing arrangement 500 capable of carrying out operations in accordance with embodiments of the invention. Those skilled in the art will appreciate that the exemplary mobile computing arrangement 500 is merely representative of general functions that may be associated with such mobile devices, and also that landline computing systems similarly include computing circuitry to perform such operations.

Figure 5:
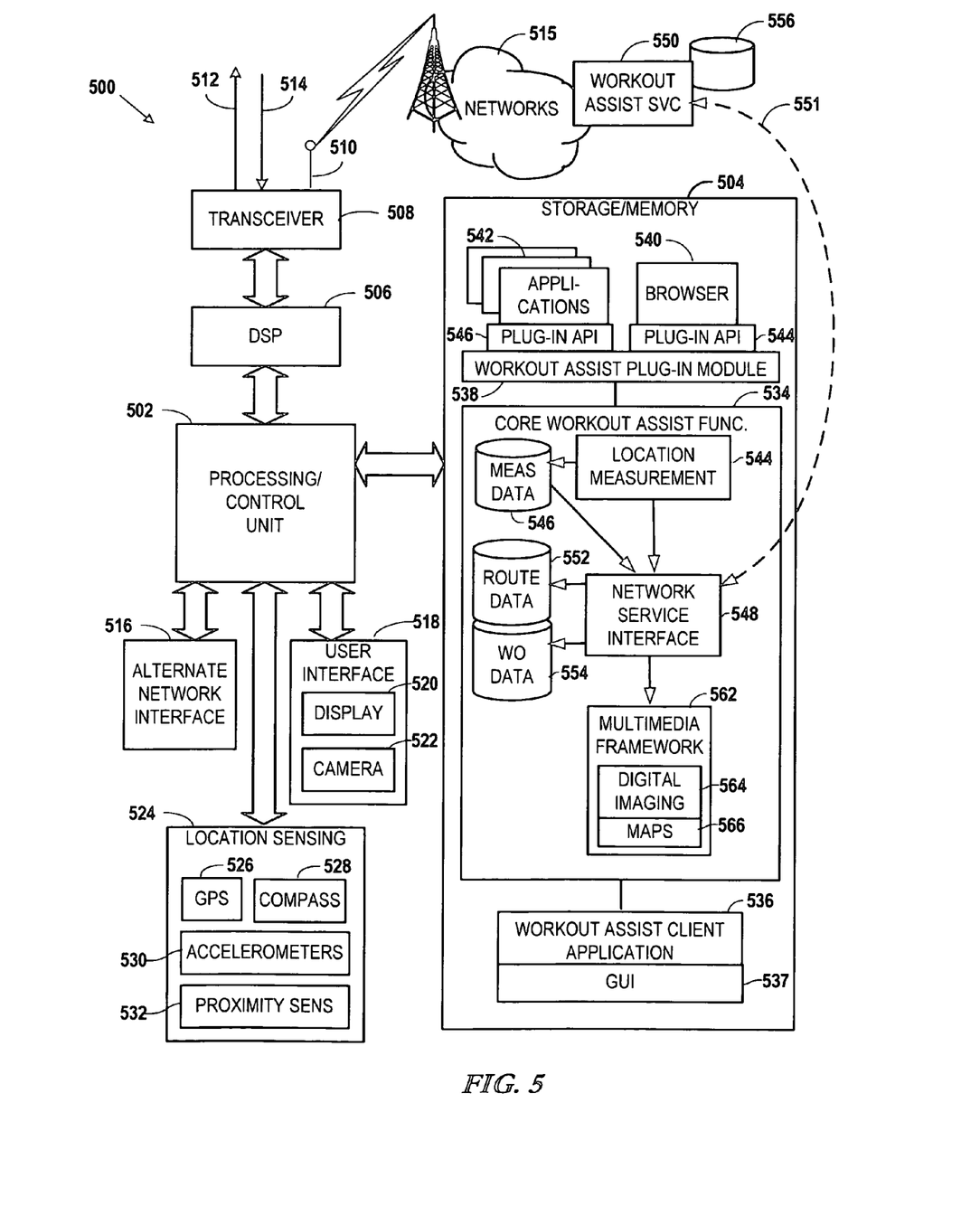
FIG. 5 is a block diagram illustrating a representative mobile computing arrangement capable of carrying out operations in accordance with embodiments of the invention.

The processing unit 502 controls the basic functions of the arrangement 500. Those functions associated may be included as instructions stored in a program storage/memory 504. In one embodiment of the invention, the program modules associated with the storage/memory 504 are stored in non-volatile electrically-erasable, programmable read-only memory (EEPROM), flash read-only memory (ROM), hard-drive, etc. so that the information is not lost upon power down of the mobile terminal. The relevant software for carrying out conventional mobile terminal operations and operations in accordance with the present invention may also be transmitted to the mobile computing arrangement 500 via data signals, such as being downloaded electronically via one or more networks, such as the Internet and an intermediate wireless network(s).

The mobile computing arrangement 500 may include hardware and software components coupled to the processing/control unit 502 for performing network data exchanges. The mobile computing arrangement 500 may include multiple network interfaces for maintaining any combination of wired or wireless data connections. In particular, the illustrated mobile computing arrangement 500 includes wireless data transmission circuitry for performing network data exchanges.

This wireless circuitry includes a digital signal processor (DSP) 506 employed to perform a variety of functions, including analog-to-digital (A/D) conversion, digital-to-analog (D/A) conversion, speech coding/decoding, encryption/decryption, error detection and correction, bit stream translation, filtering, etc. A transceiver 508, generally coupled to an antenna 510, transmits the outgoing radio signals 512 and receives the incoming radio signals 514 associated with the wireless device. These components may enable the arrangement 500 to join in one or more networks 515, including mobile service provider networks, local networks, and public networks such as the Internet.

The mobile computing arrangement 500 may also include an alternate network/data interface 516 coupled to the processing/control unit 502. The alternate network/data interface 516 may include the ability to communicate on secondary networks using any manner of data transmission medium, including wired and wireless mediums. Examples of alternate network/data interfaces 516 include USB, Bluetooth, Ethernet, 802.11 Wi-Fi, IRDA, etc. These alternate interfaces 516 may also be capable of communicating via the networks 515.

The processor 502 is also coupled to user-interface elements 518 associated with the mobile terminal. The user-interface 518 of the mobile terminal may include, for example, a display 520 such as a liquid crystal display and a camera 522. Other user-interface mechanisms may be included in the interface 518, such as keypads, speakers, microphones, voice commands, switches, touch pad/screen, graphical user interface using a pointing device, trackball, joystick, etc. These and other user-interface components are coupled to the processor 502 as is known in the art.

Other hardware coupled to the processing unit 502 includes location sensing hardware 524. Generally, the location sensing hardware 524 allows the processing logic of the arrangement 500 to determine absolute and/or relative location and orientation of the arrangement. The location may be expressed in any known format, such as lat/lon and UTM. The orientation may also be expressed using angles of a component of the arrangement (e.g., lens of the camera 522) relative to known references. For example, pitch and roll measurements may be used to define angles between the component and the earth's surface. Similarly, a heading measurement may define an angle between the component and magnetic north. The location sensing hardware 524 may include any combination of GPS receivers 526, compasses 528, accelerometers 530, and proximity sensors 532, and any other sensing technology known in the art.

In typical embodiments, the location sensing hardware 524 will at least include the GPS receiver 526, as such devices can be included at fairly low cost, and do not require any additional infrastructure other than the currently deployed satellite constellation. The location sensing hardware 524 may be integrated into the hardware packaging of the arrangement 500, or may be an add-on or peripheral device. For example, an external Bluetooth capable GPS receiver 526 may be capable of being data coupled to (and possibly physically integrated with) the arrangement 500 for purposes of providing location sensing functions described herein.

The program storage/memory 504 typically includes operating systems for carrying out functions and applications associated with functions on the mobile computing arrangement 500. The program storage 504 may include one or more of read-only memory (ROM), flash ROM, programmable and/or erasable ROM, random access memory (RAM), subscriber interface module (SIM), wireless interface module (WIM), smart card, hard drive, or other removable memory device. The storage/memory 504 of the mobile computing arrangement 500 may also include software modules for performing functions according to embodiments of the present invention.

In particular, the program storage/memory 504 includes a core functionality module 534 that provides some or all of the workout assistance client functionality as described hereinabove. The core functionality 534 may be used by a standalone workout assistant application 536 and associated graphical user interface (GUI) 537. The core functionality 534 may also be included as a workout assistance plug-in module 538. The plug-in module 538 may be used to extend the functionality of other applications such as a browser 540 or other applications 542. These applications 540, 542 have respective generic plug-in interfaces 544, 546 that allow third parties to extend the functionality of the original application 540, 542.

The core functionality module 534 includes a real-time or near-real-time location measurement module 544 that is capable of measuring locations of the arrangement 500 via the location sensing hardware 524. The location measurements may be stored in a measurement database 546 for later access. A network service module 548 is capable of using the measured data 546 with a network service 550 via the network 515, and as indicated by path 551. This service 550 may provide route data and comparative workout data for display in the GUI 537. The route and workout data may be obtained via the service 500 stored locally in respective local databases 552, 554. The GUI 537 may also have provisions for the user to create their own route data 552 and measured workout data 554 that is compatible for sharing via the service 550.

The route data 552 may be created by the user of the device 500, such as by manually entering points or using previously captured data. The workout assistant application 536 may be able to assist in this data creation, such as by presenting a user interface 537 for creating and managing the routes. The routes may also be created externally, such as on a desktop computer or via a different measuring device. In such a scenario, the core functionality module 534 may assist in downloading, verifying, and storing such externally created data on the device 500.

The network service interface 548 may include functions that allow the device 500 to download, upload, augment and search for route and workout data via the service 550. The browser 540 may serve as a convenient interface for accessing such data, and can integrate such operations with the core functionality 534 via the plug in 538. Besides allowing user access to route and workout data, the browser 540 may provide additional interactions via mechanisms known in the art, including newsgroups, imagery (e.g., route images), RSS feeds, access to databases 556, etc.

The GUI 537 may assist in rendering comparative workout data to the user in a graphical form, and this may be accomplished by way of a multimedia framework module 562. This module 562 may include such capabilities as a digital imaging component 564 that renders route data 552, workout data 554, and/or measured data 546 on the display 520 in two-dimensional and three-dimensional views. The multimedia framework 562 may also include maps 566 that can be placed in the background of rendered data. The multimedia framework 562 may also assist in other aspects of the core functionality 534. For example, the digital imaging component 564 may be able to access digital photos taken via the camera 522 and associate those photos with measured position data 546, route data 552, and/or workout data 554. This gives the users a more complete record of their workouts and travels, and the network service 550 may enable sharing such photo data.

The mobile computing arrangement 500 of FIG. 5 is provided as a representative example of a computing environment in which the principles of the present invention may be applied. From the description provided herein, those skilled in the art will appreciate that the present invention is equally applicable in a variety of other currently known and future mobile and landline computing environments. For example, desktop computing devices similarly include a processor, memory, a user interface, and data communication circuitry. Thus, the present invention is applicable in any known computing structure where data may be communicated via a network.

As described above, a network service may be able to offload some computational tasks of workout assistance, as well as allowing a community to add to and modify route and workout data. One way to do this is to provide one or more network service components that centralize and standardize various types of location-referenced data. For example, a specialized search engine may be able to parse latitudes and longitudes taken from measured data, and produce a number of known routes that are formatted to assist in producing augmented data as described herein. In reference now to FIG. 6, an example computing structure 600 is shown that may be suitable for providing workout assistance services according to embodiments of the present invention.

Figure 6:
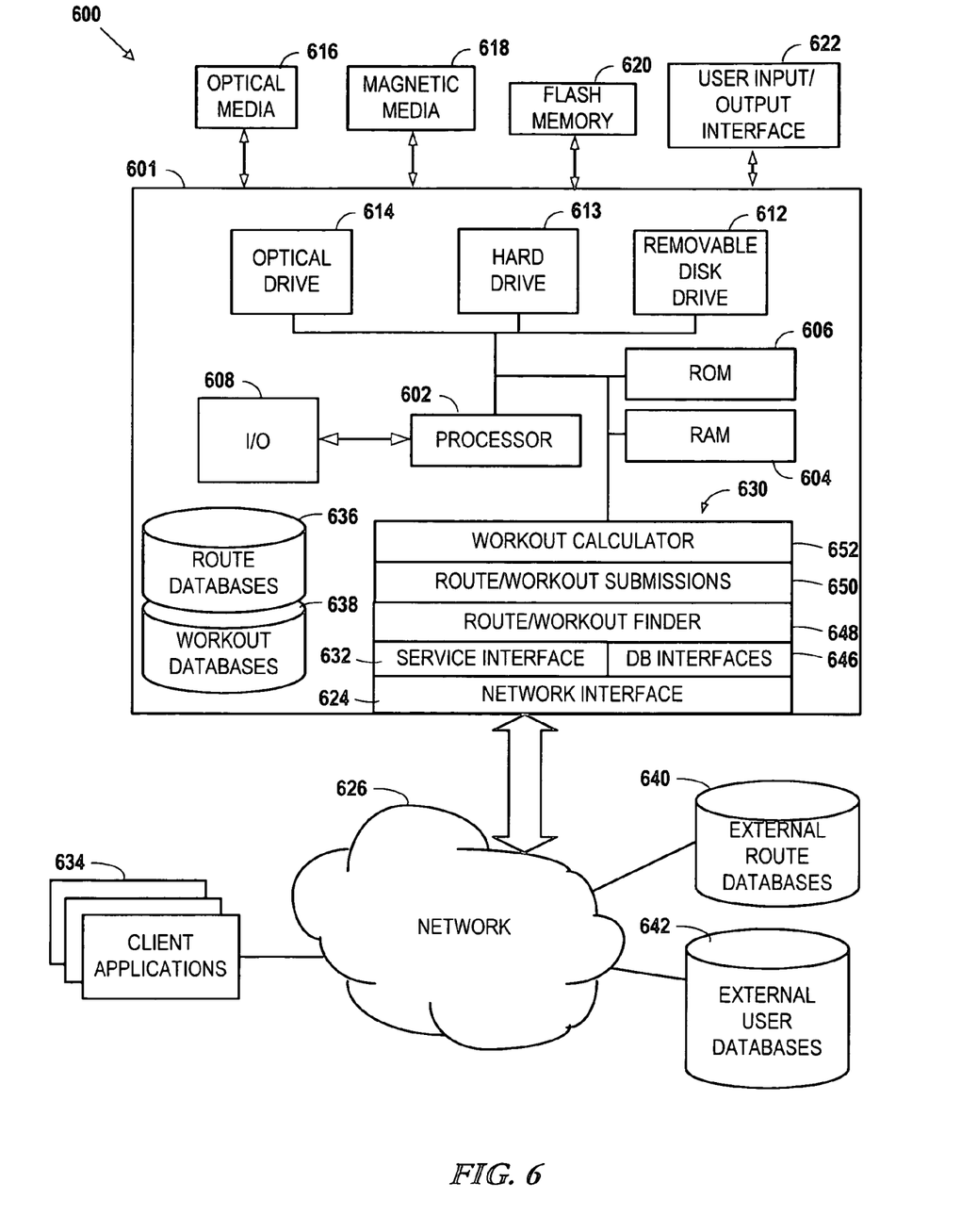
FIG. 6 is a block diagram illustrating an example computing structure suitable for providing location-aware services according to embodiments of the present invention.

The computing structure 600 includes a computing arrangement 601. The computing arrangement 601 may include custom or general-purpose electronic components. The computing arrangement 601 includes a central processor (CPU) 602 that may be coupled to random access memory (RAM) 604 and/or read-only memory (ROM) 606. The ROM 606 may include various types of storage media, such as programmable ROM (PROM), erasable PROM (EPROM), etc. The processor 602 may communicate with other internal and external components through input/output (I/O) circuitry 608. The processor 602 carries out a variety of functions as is known in the art, as dictated by software and/or firmware instructions.

The computing arrangement 601 may include one or more data storage devices, including removable disk drives 612, hard drives 613, optical drives 614, and other hardware capable of reading and/or storing information. In one embodiment, software for carrying out the operations in accordance with the present invention may be stored and distributed on optical media 616, magnetic media 618, flash memory 620, or other form of media capable of portably storing information. These storage media may be inserted into, and read by, devices such as the optical drive 614, the removable disk drive 612, I/O ports 608 etc. The software may also be transmitted to computing arrangement 601 via data signals, such as being downloaded electronically via a network, such as the Internet. The computing arrangement 601 may be coupled to a user input/output interface 622 for user interaction. The user input/output interface 622 may include apparatus such as a mouse, keyboard, microphone, touch pad, touch screen, voice-recognition system, monitor, LED display, LCD display, etc.

The computing arrangement 601 may be coupled to other computing devices via networks. In particular, the computing arrangement includes a network interface 624 for interacting with client and server entities via a network 626. The network interface 624 may include a combination of hardware and software components, including media access circuitry, drivers, programs, and protocol modules.

The computing arrangement 601 includes processor executable instructions 630 for carrying out tasks of the computing arrangement 601. These instructions include a service interface 632 capable of communicating with client applications 634 for purposes of exchanging route and workout data with the clients 634. Such data can be used for real-time comparisons of data gathered during user workouts. The service interfaces 632 are generally capable of receiving search queries from the client applications 634, such as queries directed to finding appropriate route and target workouts associated with the routes. The service interface 632 can deliver results of these queries in the form of route and workout data to the applications 634. The service interface 632 may also receive real-time measurements for purposes of calculating comparative workout data, and sending the results of those calculations to the clients 634. The service interface 632 may also include other functions sometimes associated with network services, such as managing authentication and identities, tracking statistics, providing proxy services, etc.

The computing arrangement 601 may include local route and workout database 636, 638 for accessing route and workout data accessible via a database interface 646. The computing arrangement 601 may also have access to one or more remote databases 640, 642 via the database interface 646. The external route database 640 may include, authoritative route data created by government or corporate entities for various purposes. For example, results of a government survey of an area may include high-precision location/elevation data that is useful in forming and/or augmenting route data. The user databases 642 may include data contributed from various individuals or groups, and may be in the form of a file server (e.g., FTP/HTTP), Web log ("blog"), or some other remotely accessible data service. The clients 634 may store, retrieve, view, and/or modify data stored in these databases, 636, 638, 640, 642 including route data, measured location data, route annotations, biometric data, etc.

The local databases 636, 638 typically have specialized data formats and relationships that are uniquely suited to service and the client applications 634. The remote databases 640, 642 may have similar or different formats. Where the formats are different, the database interface 646 may perform translation between the respective formats of the local databases 636, 638 and remote databases 640, 642.

One purpose of the services provided by the computing structure 600 is to provide easily locatable, properly formatted route and workout data. Therefore, a route/workout finder 648 may be able to service specialized queries for finding data on the appropriate databases 636, 638, 640, 642. In order to build these databases 636, 638, 640, 642, the service may also be able to accept submissions for adding to the databases, as represented by submissions module 650. This module 650 may accept real-time or historical submissions for inclusion in the database. This module 650 may include a verification component to check the accuracy of publicly submitted route and workout data. For example, the applications 634 may have the capability to encrypt data to ensure it is not intercepted or tampered with. In some instances where the comparisons between workouts is important (e.g., an award is associated with winning times), other verification mechanisms may also be implemented, including the capability of a disinterested witness to verify that such workout measurements were completed appropriately.

Another function provided by the service is to assist the client applications 634 in determining real time workout data comparisons. This is shown as a workout calculator module 652. The workout calculator 652 may be able to receive configurations/setups from the clients 634, receive real-time workout data from the clients 634, correct/condition the received data using route data 636 and/or numerical analysis, compare the received data against other workout data in the databases 638, 642, generate comparative statistics that are displayable in near-real time to the user via the clients 634, format and send the comparative data to the clients 634, and provide summary/end of workout statistics to the clients 634.

The computing structure 600 is only a representative example of network infrastructure hardware that can be used to provide location-based services as described herein. Generally, the functions of the computing structure 600 can be distributed over a large number of processing and network elements, and can be integrated with other services, such as Web services, gateways, mobile communications messaging, etc.

Figure 7:
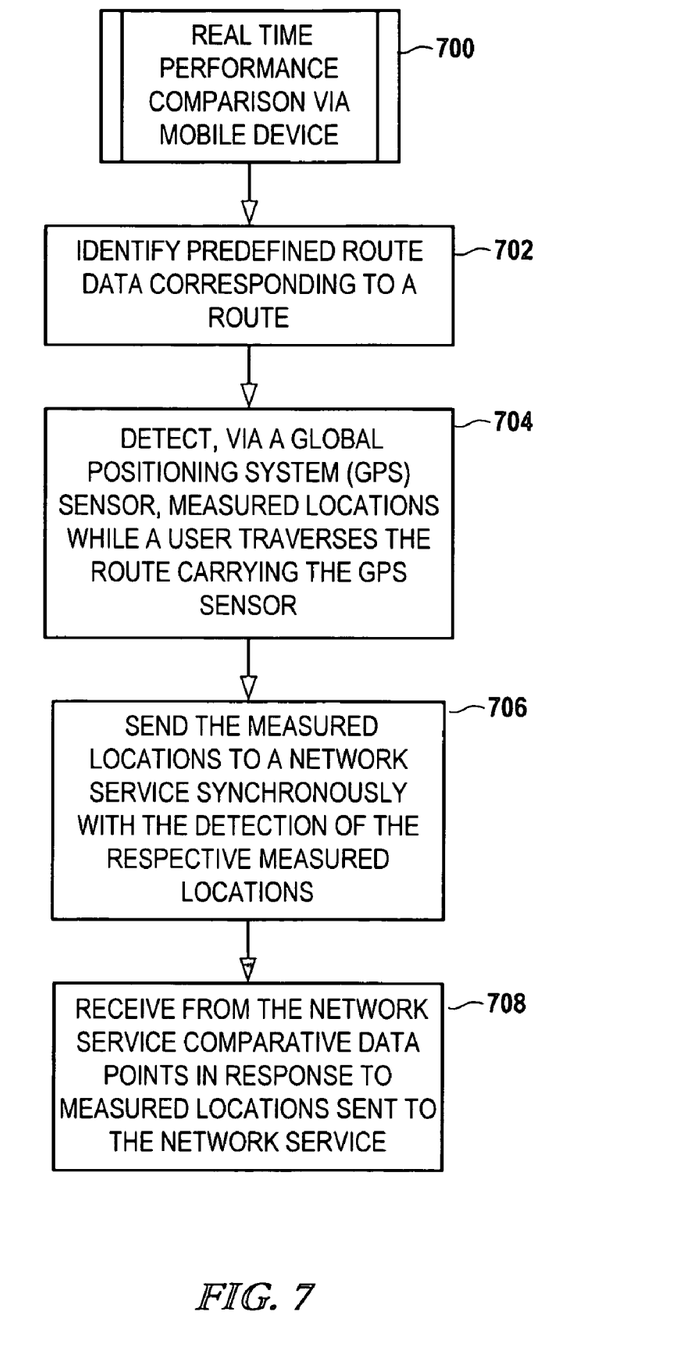
FIG. 7 is a flowchart showing-steps in providing real-time performance comparison according an embodiment of the present invention.

In reference now to FIG. 7, a flowchart illustrates a procedure 700 for real time comparison via a mobile device according to an embodiment of the invention. Predefined route data corresponding to a route is identified 702. Measured locations are detected 704, via a Global Positioning System (GPS) sensor, while a user traverses the route carrying the GPS sensor. The measured locations are sent 706 to a network service synchronously with the detection of the respective measured locations. Comparative data points are received 708 from the network service in response to measured locations sent to the network service. The comparative data points are derived based on the predefined route data and the measured locations. The comparative data points allow the user to measure relative performance during the route traversal.

Figure 8:
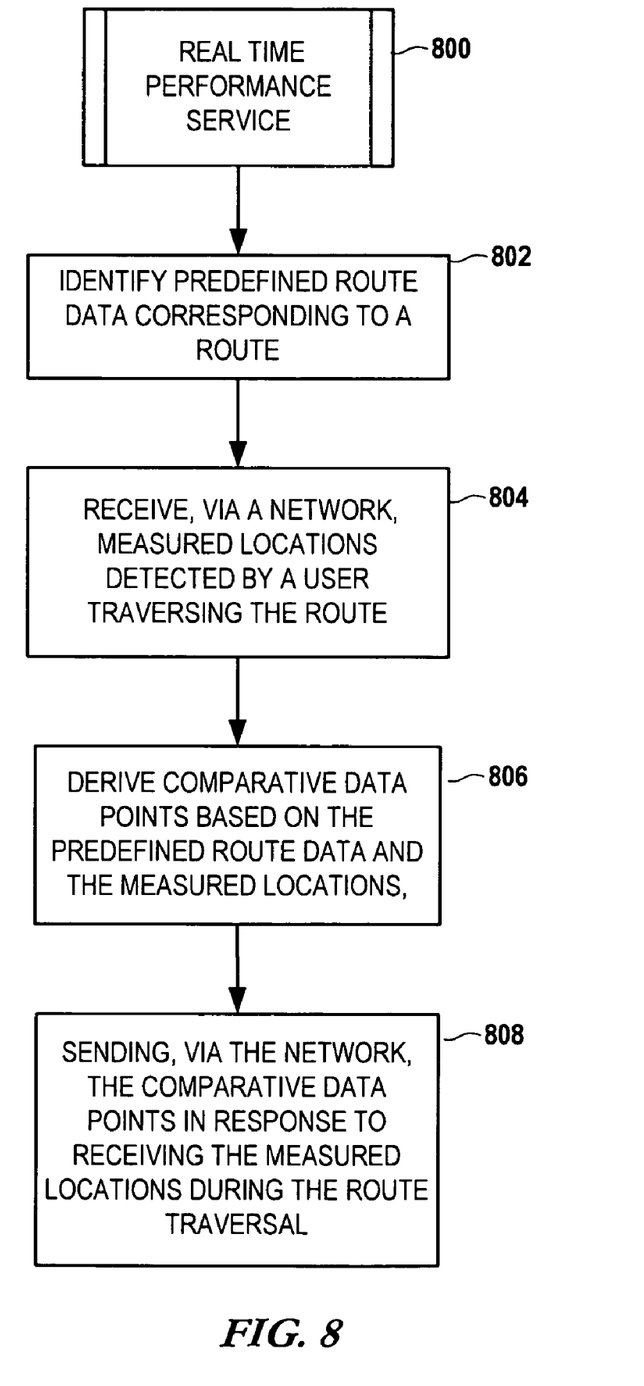
FIG. 8 is a flowchart showing steps for providing a real-time performance service according to embodiments of the present invention.

In reference now to FIG. 8, a flowchart illustrates a procedure 800 for providing a real time performance service according to an embodiment of the invention. Predefined route data corresponding to a route is identified 802. Measured locations detected by a user traversing the route are received 704 via a network. The measured locations are received synchronously with the detection of the measured locations. Comparative data points are derived 806 based on the predefined route data and the measured locations. The comparative data points allow the user to measure relative performance during the route traversal. The comparative data points are sent 808 via the network in response to receiving measured locations during the route traversal.

The foregoing description of the exemplary embodiments of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather determined by the claims appended hereto.

What is claimed is:

1. An apparatus comprising:
 at least one processor; and
 at least one memory including computer program code,
 the at least one memory and the computer program code configured to, with the at least one processor, cause the apparatus to perform at least the following,
 identify predefined route data corresponding to a route;
 determine to detect, via a location sensor, measured locations while a user traverses the route carrying the location sensor;
 determine to transmit the measured locations to a network service synchronously with the detection of the respective measured locations; and
 receive from the network service of comparative data points in response to measured locations sent to the network service, wherein the comparative data points are derived based on the predefined route data and the measured locations, and used to measure relative exercise performance during the route traversal.

2. The apparatus of claim 1, wherein the apparatus is further caused to identify the predefined route via the network service.

3. The apparatus of claim 1, wherein the route is an exercise route, the comparative data points comprises at least one of exercise statistics of the user and exercise statistics relative to one or more other users who have traversed or are traversing the route.

4. The apparatus of claim 3, further comprising a display, and wherein the apparatus is further caused to render on the display, relative locations of the user and the other users, based on the exercise statistics.

5. The apparatus of claim 3, wherein the relative exercise performance comprises rankings of the user relative to the one or more other users who have traversed or are traversing the route.

6. The apparatus of claim 1, wherein the apparatus is within a mobile device, and the apparatus is further caused to: determine to render audio representation of the comparative data points to the user via during route traversal.

7. The apparatus of claim 6, wherein the apparatus is further caused to: compare current physiological exercise statistics of the user with the exercise statistics; and determine to transmit a warning of an increased heath risk.

8. The apparatus of claim 3, wherein the one or more other users are in at least one of a selected exercise time period group, a performance level group, a selected age group, a selected weight group, and a selected sex.

9. The apparatus of claim 1, wherein the apparatus is further caused to: compare current physiological exercise statistics of the user with exercise statistics of a selected animal or machine.

10. The apparatus of claim 1, wherein the apparatus is further caused to: download, upload, augment and search for the predefined route and the exercise statistics via a dedicated service.

11. The apparatus of claim 3, wherein the apparatus is further caused to:

receive a selection of a target exercise performance on the route based upon the exercise statistics; and determine to display an instruction to slow down or speed up based upon comparison between performance of the user and the target exercise performance.

12. The apparatus of claim 11, wherein the apparatus is further caused to:

determine to display an alert to stop or turn back, when the user is not able to finish the route or to finish the route with an intensity level in line with the target exercise performance, wherein the comparison is based upon intensity measurement of at least one of an average heart rate, a workout type, and an exercise type.

13. An apparatus comprising:

at least one processor; and at least one memory including computer program code, the at least one memory and the computer program code configured to, with the at least one processor, cause the apparatus to perform at least the following, identify predefined route data corresponding to a route;

receive by a network service measured locations from a mobile device synchronously with the detection of the measured locations by the mobile device;

derive comparative data points based on the predefined route data and the measured locations, wherein the comparative data points are used to measure relative exercise performance during the route traversal; and determine to transmit the comparative data points from the network service to the mobile device during the route traversal.

14. The apparatus of claim 13, wherein the route is an exercise route, and the apparatus is further caused to derive the comparative data points by deriving statistics relative to one or more other users who have traversed or are traversing the route.

15. The apparatus of claim 13, wherein the relative exercise performance comprises rankings of the user relative to the one or more other users who have traversed or are traversing the route.

* * * * *